United States Patent [19]

Riesser

[11] 4,098,723
[45] * Jul. 4, 1978

[54] CATALYST FOR DEHYDROGENATION

[75] Inventor: Gregor H. Riesser, Houston, Tex.

[73] Assignee: Shell Oil Company, Houston, Tex.

[*] Notice: The portion of the term of this patent subsequent to Oct. 4, 1994, has been disclaimed.

[21] Appl. No.: 763,180

[22] Filed: Jan. 27, 1977

[51] Int. Cl.$^2$ .................. B01J 23/78; B01J 23/84
[52] U.S. Cl. ............................... 252/474; 260/669 R
[58] Field of Search .................. 252/474; 260/669 R

[56] References Cited

U.S. PATENT DOCUMENTS

| | | | |
|---|---|---|---|
| 2,666,086 | 1/1954 | Pitzer | 252/474 X |
| 3,654,181 | 4/1972 | Sutherland et al. | 252/474 X |

*Primary Examiner*—W. J. Shine

[57] ABSTRACT

Iron-potassium-vanadium-cobalt oxide catalysts are useful in the dehydrogenation of hydrocarbons to the corresponding more-unsaturated hydrocarbons and result in an improved yield.

16 Claims, No Drawings

CATALYST FOR DEHYDROGENATION

BACKGROUND OF THE INVENTION

1. Field of the Invention

This invention relates to improved catalysts for the dehydrogenation of hydrocarbons to corresponding more-unsaturated hydrocarbons, more particularly, to the production of vinyl aromatic hydrocarbons from alkyl aromatic hydrocarbons and to the production of olefins from the corresponding more-saturated aliphatic hydrocarbons.

2. The Prior Art

The vinyl benzenes and butadienes play a particularly important role in the preparation of synthetic rubbers, plastics and resins. The polymerization of styrene for example with various comonomers such as butadiene to produce synthetic rubbers is well known as is the polymerization of styrene to produce polystyrene resins.

Styrene and butadiene are typically produced from ethyl benzene and butylene, respectively, by dehydrogenation over solid catalysts in the presence of steam, and at temperatures ranging from 500° to 700° C. The class of catalysts found to be the most effective for this process is a potassium oxide (carbonate) promoted, chromium oxide stabilized, iron oxide material. Considerable research has gone into attempting to improve the activity and selectivity of this class of catalysts. Any improvement which results in either increasing the selectivity (moles of desired product produced per mole of reactant reacted) or the conversion (moles of reactant reacted per mole of starting material) without lowering the other is economically attractive since the result is that the yield (moles of desired product produced per mole of reactant) of the product has been increased. Any increase in the numerical value of the yield results in a more efficient operation with more reactant being converted into the desired product. In commerical operations many of which produce millions of pounds of product per year, an increase of only 1 or 2 percentage points in the selectivity or yield can result in a substantial net increase in the plant production or a substantial savings of starting materials.

The addition of vanadium pentoxide is known to improve the selectivity of the above described iron-chromium-potassium oxide catalysts. Such catalysts containing vanadium pentoxide were desclosed in U.S. Pat. No. 3,361,683 to W.R. Gutmann, issued Jan. 2, 1968 or U.S. Pat. No. 3,084,125 to F.J. Soderquist, issued Apr. 2, 1963.

Addition of cobalt to a typical iron-chromium-potassium oxide catalyst has been disclosed in U.S. Pat. No. 3,291,756 to R.S. Bowman, issued Dec. 13, 1966. In copending applications Ser. Nos. 740,262 now U.S. Pat. No. 4,052,338, and 740,264 filed Nov. 8, 1976, the addition of cobalt and vanadium to iron-chromium potassium oxide catalysts is taught.

Commercial iron-oxide based potassium catalysts typically utilize chromium oxide as structural stabilizers. P. H. Lee in CATALYSIS REVIEWS 8 (2) at page 295 (1973) notes that removing chromium oxide from alkali-promoted iron oxide catalysts results in a very rapid loss in activity in only a few hours. It has been found that the addition of cobalt and vanadium compounds to potassium promoted iron oxide based catalysts results in catalysts which do not exhibit such rapid activity loss.

STATEMENT OF INVENTION

It has now been found that when small amounts of cobalt and vanadium compounds are added to dehydrogenation catalysts comprising iron oxide and potassium oxide/carbonate, the yield to unsaturated hydrocarbons from corresponding more-saturated materials is improved. In particular, yield to styrene from ethylbenzene and butadiene from butylene is improved. In particular, the catalyst of this invention is useful for the production of olefins from the corresponding more-saturated aliphatic hydrocarbons, and specifically for the production of butadiene from butylene or isoprene from amylene. The catalyst of this invenion is further of use in producing alkenyl aromatic hydrocarbons from alkyl aromatic hydrocarbons particularly lower alkenyl aromatic hydrocarbons from lower alkyl aromatic hydrocarbons as for example, ethyl benzene, isopropylbenzene, diethylbenzene and ethyl methyl benzene, where the lower alkenyl and lower alkyl groups have from two to six carbon atoms, and specifically is useful for the production of styrene from ethyl benzene.

DETAILED DESCRIPTION OF THE INVENTION

The catalysts of this invention typically contain (a) from about 50 to about 95 and preferably from about 55 to about 90 percent by weight of iron compound, measured as ferric oxide, (b) from about 5 to about 30 and preferably from about 6 to about 25 percent by weight of potassium compound, measured as potassium oxide, (c) from about 1 to about 6 and preferably from about 2 to about 5 percent by weight of vanadium compound measured as vanadium pentoxide and (d), from about 0.01 to about 10, preferably from about 0.1 to about 10, more preferably from about 0.1 to about 5, even more preferably from about 0.3 to about 4, and most preferably from about 0.5 to about 3 percent by weight of a cobalt compound measured as cobaltous oxide. Alternately stated, these catalysts contain (a) from about 35 to about 67 and preferably from about 38 to about 63 percent by weight of an iron oxide, measured as iron metal, (b) from about 4 to about 25 and preferably from about 5 to about 21 percent by weight of a potassium compound, measured as potassium metal, (c) from about 0.5 to about 3.5 and preferably from about 1 to about 3 percent by weight of a vanadium oxide measured as vanadium metal and (d) from about 0.0075 to about 8, preferably from about 0.075 to about 8, more preferably from about 0.075 to about 4, even more preferably from about 0.2 to about 3.5, and most preferably from 0.35 to about 2.5 percent by weight of a cobalt oxide measured as cobalt metal.

Variances within the general composition described above depend in part on whether the catalyst is used to produce vinyl aromatic compounds or olefinic compounds.

Catalysts for the production of vinyl aromatic compounds such as styrene from ethyl benzene and alpha-methylstyrene from cumene typically contain from about 75 to about 95 and preferably from about 80 to about 90 percent by weight of iron compound measured as ferric oxide, from about 5 to about 20 and preferably from about 6 to about 25, more preferably from about 6 to about 15 percent by weight of potassium compound measured as potassium oxide, from about 1 to about 6 and preferably from about 2 to 5 percent by weight of vanadium compound measured as vanadium pentoxide and from about 0.01 to about 10, preferably from about 0.1 to about 10, more preferably from about 0.1 to about 5, even more preferably from about 0.3 to about 4 and most preferably from about 0.5 to about 3 percent by weight of a cobalt compound measured as cobaltous oxide. Alternatively stated, these catalysts contain from about 52 to about 67 and preferably from about 56 to about 63 percent by weight of an iron oxide measured as iron metal, from about 5 to about 21, more preferably from about 4 to about 17 and preferably from about 5 to about 13 percent by weight of a potassium compound measured as potassium metal, from about 0.5 to about 3.5 and preferably from about 1 to about 3 by weight of a vanadium oxide measured as vanadium metal and from about 0.0075 to about 8, preferably from about 0.075 to about 8, more preferably from about 0.075 to about 4, even more preferably from about 0.2 to about 3.5 and most preferably from about 0.35 to about 2.5 percent by weight of cobalt oxide measured as the metal.

Catalysts for the production of dienes from mono-olefins such as, for example, isoprene from amylene or butadiene from butylene typically contain from about 50 to about 75 and preferably from about 55 to about 70 percent by weight of iron compound measured as ferric oxide, from about 15 to about 30 and preferably from about 20 to about 30 percent by weight of potassium compound measured as potassium oxide, from about 1 to about 6 and preferably from about 2 and about 5 percent by weight of vanadium compound measured as vanadium pentoxide and from about 0.01 to about 10, preferably from about 0.1 to about 10, more preferably from about 0.1 to about 5, even more preferably from about 0.3 to about 5, yet even more preferably from about 0.3 to about 4.0 and most preferably from about 0.5 to about 3 percent by weight of a cobalt compound measured as cobaltous oxide. Alternatively stated, these catalysts contain from about 35 to about 53 and perferbably from about 38 to about 49 percent by weight of an iron oxide measured as an iron metal, from about 12 to about 25 and preferably from about 16 to about 25 percent by weight of a potassium compound measured as potassium metal, from about 0.5 to about 3.5 and preferably from about 1 to about 3 percent by weight of a vanadium oxide measured as vanadium metal, and from about 0.0075 to about 8, preferably from about 0.075 to about 8, more preferably from about 0.075 to about 4, even more preferably from about 0.2 to about 4, yet even more preferably from about 0.2 to about 3.5, and most preferably from about 0.35 to about 2.5 percent by weight of a cobalt oxide measured as cobalt metal.

It is known that the most selective catalysts are those having surface areas below 10 sq. meter per gram, and in many cases below 5 sq. meter/gram. If iron oxides have surface areas in excess of this requirement the surface area can be reduced by precalcining the iron oxides at temperatures exceeding 700° C for a period of time ranging from one-half hour to several hours.

The strength of the catalysts can be improved by adding binding agents such as calcium aluminate and Portland cement. However, catalyst strength can also be improved by calcining the extruded pellets at temperatures ranging from about 700° to about 1000° C. Calcination at these temperatures can alleviate the use of binding agents.

While most of the above methods result in catalysts having desired surface area, they also result in catalysts having a relatively high density. It has been found that catalysts having a highly porous structure and a low surface area are highly active in catalytic dehydrogenation. Various methods have been employed to form highly porous catalysts. For example, combustible materials, such as sawdust, carbon, wood flour, etc., have been added during catalyst formation, and then burned out after the pellet has been formed. Many of these porosity-promoting aids also assist in facilitating extrusion of pellets, for example, the use of graphite and aqueous solutions of methyl cellulose.

Many forms of iron oxide can be used in preparation of the catalyst of this invention. Typically, iron oxides employing catalyst preparations of this sort are usually a synthetically produced, powdered red, red-brown, yellow or black pigment. The red or red-brown pigments are highly pure ferric oxide, while the black pigment is the magnetic form, ferrosoferric oxide ($Fe_3O_4$), which is usually found in the catalyst under various reaction conditions. The yellow iron oxides consist of the monohydrated form of ferric oxide. These oxides are prepared by various methods, e.g., oxidation of iron compounds, roasting, precipitation, calcination, etc. A suitable form of iron compound is the monohydrated yellow iron oxide used in the preparation of catalysts according to U.S. Pat. No. 3,360,597, issued Dec. 26, 1967, and U.S. Pat. No. 3,364,277, issued Jan. 16, 1968. Particularly suitable are pigment grade red iron oxides of purities exceeding 98% wt. These red oxides have surface areas ranging from 2 to 50 $m^2$/gram and particle sizes from 0.1 to 2 microns. The iron compound is present in the catalyst in either one or a mixture of both of its possible oxidation, states, i.e., as ferrous iron or ferric iron or mixtures thereof as for example ferrosoferric iron. The iron compound present is conveniently measured ferric oxide.

The potassium promoter is added to the catalyst in various forms. For example, it may be added as the oxide, or as other compounds which are convertible, at least in part, under calcination conditions, to the oxides, such as the hydroxides, the carbonates, the bicarbonates, the phosphates, the borates, the acetates, and the like. A particularly preferred potassium compound is potassium carbonate. The potassium compound is present in the catalyst as a potassium oxide, a potassium carbonate or a mixture thereof. High carbon dioxide partial pressures in the reaction gases will favor higher carbonate to oxide ratios and vice versa. The potassium compound(s) is conveniently measured as potassium oxide.

Vanadium is added to the catalyst as vanadium pentoxide or as salts or other compounds thermally decomposable to the oxides, such as sulfates, oxysulfates, sulfides, or vanadates. The vanadium is present in the catalyst in one or mixtures of more than one of its possible oxidation states, the pentavalent state being the preferred state. The vanadium compound(s) is conveniently measured as the vanadium pentoxide.

Cobalt is added to the catalyst as the oxide, or as compounds decomposable to the oxide such as hydroxides, nitrates, acetates, oxalates, and the like. The cobalt is present in the catalyst in the cobaltous or cobaltic oxidation state or mixtures thereof. The cobalt compound(s) is conveniently measured as the cobaltous oxide.

The catalyst of this invention will consist of mixtures of oxides, both simple oxides such as ferric oxide and complex oxides such as the spinels and ferrites as well as oxides such as vanadates, etc., and carbonates, with carbonates of potassium preferred. Specific oxides present in the calcined catalyst will be determined by calcining conditions, reaction conditions, etc. Typical calcining conditions range from about 500° to about 1100° C. Since typical commercial dehydrogenation reactions are carried out in the presence of steam and carbon dioxide, the catalyst contains a proportion of carbonates. The catalyst of this invention comprises a mixture of oxides and carbonates having from about 50 to about 95 percent by weight of an iron oxide, measured as ferric oxide; from about 5 to about 30 percent by weight of a potassium compound selected from the group consisting of a potassium oxide, a potassium carbonate, or mixtures thereof, measured as potassium oxide; from about 1 to about 6 percent by weight of a vanadium oxide, measured as vanadium pentoxide, and from about 0.01 to about 10 percent by weight of a cobalt compound, measured as cobaltous oxide.

The catalyst of this invention is compounded in a variety of ways. One method is to ballmill together a mixture of the desired oxides, adding a small amount of water, and extruding the paste formed to produce small pellets, which are then dried and calcined at temperatures above 500° C. Another method is to dissolve the components together, spray dry these components to form a resulting powder, calcine the powder into the resultant oxides, and then add sufficient water to form a paste and extrude into pellets, dry and calcine. Another procedure would involve percipitation those materials which are precipitatable, such as iron, as the resultant hydroxides, partially de-watering the resultant precipitate, adding soluble salts of potassium and vanadium, and then subsequently extruding, drying and calcining the resultant pellets. A pelleting mill could also be used to form the pellets. A preferred method is to dryblend powders of iron oxide, cobalt carbonate and vanadium pentoxide, and potassium carbonate, add water, optionally containing potassium carbonate in solution, and then mull and pelletize the mixture, subsequently substantially drying and then calcining the pellets at a temperature ranging from about 600° to about 1000° C to form the final product. Alternatively, the vanadium pentoxide is dissolved in the potassium carbonate solution, rather than dry-mixed with the iron oxide, and cobalt carbonate. An alterate process for preparing the catalyst is where iron, potassium, vanadium and cobalt compounds are combined with water to from a paste, the paste mulled and formed into pellets, substantially all the water is removed from the pellets in a drying step and the pellets are calcined at a temperature ranging from about 600° to 1000° C. The drying and calcining steps can be combined into one sequential step still within the scope of this invention in a furnace whose temperature is suitably programable such as by varying the heat input or the residence time of the pellets through the furnace.

The optimum size of the pellets produced will vary according to the need of various processes. Catalyst pellets having a diameter of from ⅛ to ⅜ of an inch, and from ⅛ to ⅜ of an inch in length are typical. The smaller diameter catalysts are generally more active but provide increased pressure drops.

The dehydrogenation reaction is usually carried out at reaction temperatures of about 500°–700° C. However, higher or lower temperatures may be used without departing from the scope of this invention. The use of atmospheric, sub-atmospheric, or super-atmospheric pressure is suitable. However, it is preferable to operate at as low a pressure as is feasible, and atmospheric or subatmospheric pressure is preferred. The process of the invention may be carried out in batch, semi-continuous, or continuous operation, with continuous operation being preferred. The catalyst is employed in the form of a fixed bed, or in fluidized or suspended form. It is preferable to utilize a fixed bed. The reaction may be carried out in single stage reactors or by staging in series reactors. The reactors may be of various designs, e.g., downflow reactors, radial reactors, etc.

With the use of the catalyst of this invention, it is desirable to add steam to the reactant feed to aid in the removal of carbonaceous residues from the catalyst. The reaction feed contains from 2–30 moles of steam for every mole of feed. Catalysts having higher potassium contents are usually employed at lower feed to steam ratios. Feed to steam ratios of from about 1:9 to about 1:18 are desirable. Good results are obtained with feed to steam ratios of about 1:12.

The contact time of the reactant gas with the catalyst is usually defined in terms of gaseous-hourly-space velocity (volumes of hydrocarbon reactant per volume of catalyst per hour, i.e., GHSV). The GHSV according to this invention may vary from about 10 to 3,000 and is preferably adjusted within this range to effect the degree of conversion desired for the particular feed in question.

The preparation of catalysts, according to the invention, and their use will be further described by the following illustrative embodiments which are provided for illustration and are not to be construed as limiting the invention. It should be noted that advantages resulting from increases of selectivity of only one or two percentage points are extremely significant in a commercial process which may produce many hundreds of thousand pounds of product a day.

ILLUSTRATIVE EMBODIMENTS

Part A. A catalyst in accord with this invention was prepared by dry-blending cobaltous carbonate, vanadium pentoxide, potassium carbonate with red iron oxide having a surface area of $5m^2/gm$ and an average particle size of 1 micron. Water is then added and the mixture is mulled and pelleted. The pellets were dried at 200° C for ⅓ of an hour and then calcined at about 1000° C for about 50 minutes. This catalyst is denoted as A in Table I which gives the resultant composition. This catalyst was tested for activity and selectivity in the dehydrogenation of ethylbenzene of styrene by placing the catalyst pellets in a fixed reactor having a volume of 100 cc and passing a preheated mixture of steam and ethylbenzene at a molar ratio of 12:1 into the catalyst bed which was maintained at the temperature needed to effect the desired conversion of ethylbenzene. This temperature is dependent upon the activity of the catalyst. A pressure of about 0 to 1.5 inches of water was used and the liquid hourly space velocity of ethylbenzene was varied from about 0.65 to about $1.8h^{-1}$. The effluent vapors were analyzed for styrene, ethylbenzene, benzene and toluene. These results were converted to activity and selectivity and are recorded in Table 1.

Part B. A catalyst composition not in accord with this invention was prepared and tested in a manner similar to that of catalyst Part A above. This catalyst contains, in addition to the components of catalyst A, chromic oxide which was dry blended with the other components. Two of these catalyst, noted as B and C and their test results are shown in Table I.

In table I and hereinafter $T_{(70)}$ is used to represent the temperature of ° C at 70 percent conversion, and $S_{(70)}$ is used to represent the selectivity of 70 percent conversion. $T_{(70)}$ is the indicium of activity, the higher the temperature, the lower the activity.

TABLE I:

| Catalyst | %K$_2$O | %Cr$_2$O$_3$ | %V$_2$O$_5$ | %CoO | %Fe$_2$O$_3$ | Run Time | $T_{(70)}$ | $S_{(70)}$ |
|---|---|---|---|---|---|---|---|---|
| A | 12.6 | 0 | 3.0 | 1.6 | Bal. | 1 day(s) | 610° C | — |
|   |      |   |     |     |      | 2 day(s) | 607° | — |
|   |      |   |     |     |      | 4 day(s) | 606° C | — |
|   |      |   |     |     |      | 5 day(s) | 605° C | — |
|   |      |   |     |     |      | 6 day(s) | 606° C | 92.1 |
| B | 12.6 | 1.2 | 3.0 | 1.6 | Bal. | 2 day(s) | 608° C | — |
|   |      |   |     |     |      | 3 day(s) | 606° C | — |
|   |      |   |     |     |      | 4 day(s) | 605° C | — |
|   |      |   |     |     |      | 5 day(s) | 606° C | — |
|   |      |   |     |     |      | 6 day(s) | 605° C | 92.0 |
| C | 12.6 | 2.45 | 3.0 | 1.6 | Bal. | 6 day(s) | 609° C | — |
|   |      |   |     |     |      | 7 day(s) | 607° C | — |
|   |      |   |     |     |      | 8 day(s) | 606° C | — |
|   |      |   |     |     |      | 9 day(s) | 608° C | — |
|   |      |   |     |     |      | 10 day(s) | 608° C | 91.1 |

From Table I it can be seen that a cobalt-vanadium promoted potassium/iron oxide catalyst gives results comparable to a catalyst containing chromium oxide.

What is claimed is:

1. A catalyst for the dehydrogenation of hydrocarbons to more unsaturated hydrocarbons comprising a mixture having:
   (a) from about 35 to about 67 percent by weight of an iron oxide, measured as iron metal;
   (b) from about 4 to about 25 percent by weight of potassium oxide, measured as potassium metal;
   (c) from about 0.5 to about 3.5 percent by weight of a vanadium oxide, measured as vanadium metal; and
   (d) from about 0.0075 to about 8 percent by weight of a cobalt oxide measured as cobalt metal.

2. The catalyst of claim 1 wherein the cobalt oxide ranges from about 0.075 to about 8 percent by weight.

3. The catalyst of claim 1 wherein the hydrocarbon is a monoolefin, the more unsaturated hydrocarbon is a diene, the iron oxide ranges from about 35 to about 53 percent by weight, and the potassium oxide ranges from about 12 to about 25 percent by weight.

4. The catalyst of claim 3 wherein the cobalt oxide ranges from about 0.075 to about 8 percent by weight.

5. The catalyst of claim 4 wherein the cobalt oxide ranges from about 0.075 to about 4 percent by weight.

6. The catalyst of claim 3 wherein the mono-olefin is butylene and the diene is butadiene.

7. The catalyst of claim 6 wherein the cobalt oxide ranges from about 0.075 to about 8 percent by weight.

8. The catalyst of claim 1 wherein the hydrocarbon is an alkyl aromatic hydrocarbon, and the more unsaturated hydrocarbon is an alkenyl aromatic hydrocarbon, the iron oxide ranges from about 52 to about 67 percent by weight, and the potassium oxide ranges from about 5 to about 21 percent by weight.

9. The catalyst of claim 8 wherein the cobalt oxide ranges from about 0.075 to about 8 percent by weight.

10. The catalysts of claim 8 wherein the alkyl aromatic hydrocarbon is ethylbenzene and the alkenyl aromatic hydrocarbon is styrene.

11. The catalyst of claim 10 wherein the cobalt oxide ranges from about 0.075 to about 8 percent by weight.

12. The catalyst of claim 11 wherein the cobalt oxide ranges from about 0.075 to about 4 percent by weight.

13. The process for preparing the catalyst of claim 1 wherein iron, potassium, vanadium and cobalt oxides or compounds thermally decomposable to oxides upon calcination are combined with water to form a paste, the paste is formed into pellets, the pellets are dried and then calcined at a temperature ranging from about 600° to about 1000° C.

14. The process of claim 13 wherein the drying and calcining are performed sequentially in one step.

15. The process for preparing the catalyst of claim 2 wherein iron, potassium, vanadium and cobalt oxides or compounds thermally decomposable to oxides upon calcination are combined with water to form a paste, the paste is formed into pellets, the pellets are dried and then calcined at a temperature ranging from about 600° to about 1000° C.

16. The process of claim 15 wherein the drying and calcining are performed sequentially in one step.

* * * * *